(12) United States Patent
Beneyto-Ferre et al.

(10) Patent No.: US 11,358,029 B2
(45) Date of Patent: Jun. 14, 2022

(54) SYSTEM FOR CARRYING OUT A TRAINING OR A COMPETITION OF OR BETWEEN TWO ATHLETES

(71) Applicant: PUMA SE, Herzogenaurach (DE)

(72) Inventors: Jordi Beneyto-Ferre, Nuremberg (DE); Baljinder Kaur Miles, Herzogenaurach (DE); Charles Johnson, Nuremberg (DE)

(73) Assignee: PUMA SE, Herzogenaurach (DE)

( * ) Notice: Subject to any disclaimer, the term of this patent is extended or adjusted under 35 U.S.C. 154(b) by 0 days.

(21) Appl. No.: 16/484,225

(22) PCT Filed: Feb. 8, 2017

(86) PCT No.: PCT/EP2017/000171
§ 371 (c)(1),
(2) Date: Aug. 7, 2019

(87) PCT Pub. No.: WO2018/145719
PCT Pub. Date: Aug. 16, 2018

(65) Prior Publication Data
US 2020/0030663 A1 Jan. 30, 2020

(51) Int. Cl.
*A63B 24/00* (2006.01)
*A63B 69/00* (2006.01)
(Continued)

(52) U.S. Cl.
CPC ...... *A63B 24/0084* (2013.01); *A63B 24/0087* (2013.01); *A63B 69/0028* (2013.01);
(Continued)

(58) Field of Classification Search
CPC ............ A63B 24/0084; A63B 24/0062; A63B 24/0021; A63B 2024/0025;
(Continued)

(56) References Cited

U.S. PATENT DOCUMENTS

| | | | |
|---|---|---|---|
| 8,172,658 B2 * | 5/2012 | Svensson | G01S 19/19 702/155 |
| 9,333,411 B2 | 5/2016 | Aibara | |

(Continued)

FOREIGN PATENT DOCUMENTS

| | | |
|---|---|---|
| EP | 2283379 B1 | 3/2014 |
| JP | 2013146557 A | 8/2013 |
| JP | 2014045782 A | 3/2014 |
| WO | 2016074689 A1 | 5/2016 |

*Primary Examiner* — Nyca T Nguyen
*Assistant Examiner* — Zachary T Moore
(74) *Attorney, Agent, or Firm* — Lucas & Mercanti, LLP; Klaus P. Stoffel

(57) ABSTRACT

A system for carrying out a training or a competition of or between two athletes, wherein the system comprises: a first sports garment comprising a first signal element and a connection to a first mobile phone, wherein first control and/or calculating means are arranged for measuring of an actual distance covered by the first athlete; a second sports garment comprising a second signal element and a connection to a second mobile phone, wherein second control and/or calculating means are arranged for measuring of an actual distance covered by the second athlete, wherein first control means are provided for emitting a predetermined first signal by the first signal element in the case that the actual distance of the first athlete is bigger than the actual distance of the second athlete and wherein second control means are provided at or in the second sports garment for emitting a predetermined second signal by the second signal element in the case that the actual distance of the first athlete is bigger than the actual distance of the second athlete. So, a competition between two athletes can be carried out with an easy observation of the actual performance of the athletes.

12 Claims, 3 Drawing Sheets

(51) Int. Cl.
  *A63B 71/06* (2006.01)
  *G01C 22/00* (2006.01)
(52) U.S. Cl.
  CPC .. *A41D 2600/10* (2013.01); *A63B 2024/0093* (2013.01); *A63B 2071/0661* (2013.01); *A63B 2220/12* (2013.01); *A63B 2225/50* (2013.01); *G01C 22/00* (2013.01)
(58) Field of Classification Search
  CPC ...... A63B 2024/0068; A63B 2071/065; A63B 2071/0658; A63B 2071/0661; A63B 2071/0663; A63B 2071/0666; A63B 2220/10; A63B 2220/12; A63B 2220/13; A63B 2225/50; A63B 2225/52; A63B 2225/54; A61B 5/1116; A61B 5/1118; A61B 5/1121; A41D 2600/10; A41D 1/002; A41D 1/005; A41D 27/085; A41D 27/205
  See application file for complete search history.

(56) References Cited

U.S. PATENT DOCUMENTS

| | | | |
|---|---|---|---|
| 9,750,976 B2 | 9/2017 | Weast | |
| 2003/0137852 A1* | 7/2003 | Rapisarda | A41D 13/01 362/570 |
| 2011/0277206 A1* | 11/2011 | Sokolowski | A61B 5/02438 600/509 |
| 2012/0015778 A1* | 1/2012 | Lee | A63B 71/0686 482/8 |
| 2012/0183940 A1* | 7/2012 | Aragones | A61B 5/744 434/247 |
| 2013/0106684 A1* | 5/2013 | Weast | A61B 5/6831 345/156 |
| 2014/0343843 A1* | 11/2014 | Yanku | G01C 21/20 701/491 |
| 2016/0158623 A1* | 6/2016 | Morehouse | A63B 69/02 273/148 R |
| 2019/0060736 A1* | 2/2019 | Harris | H04W 4/80 |

* cited by examiner

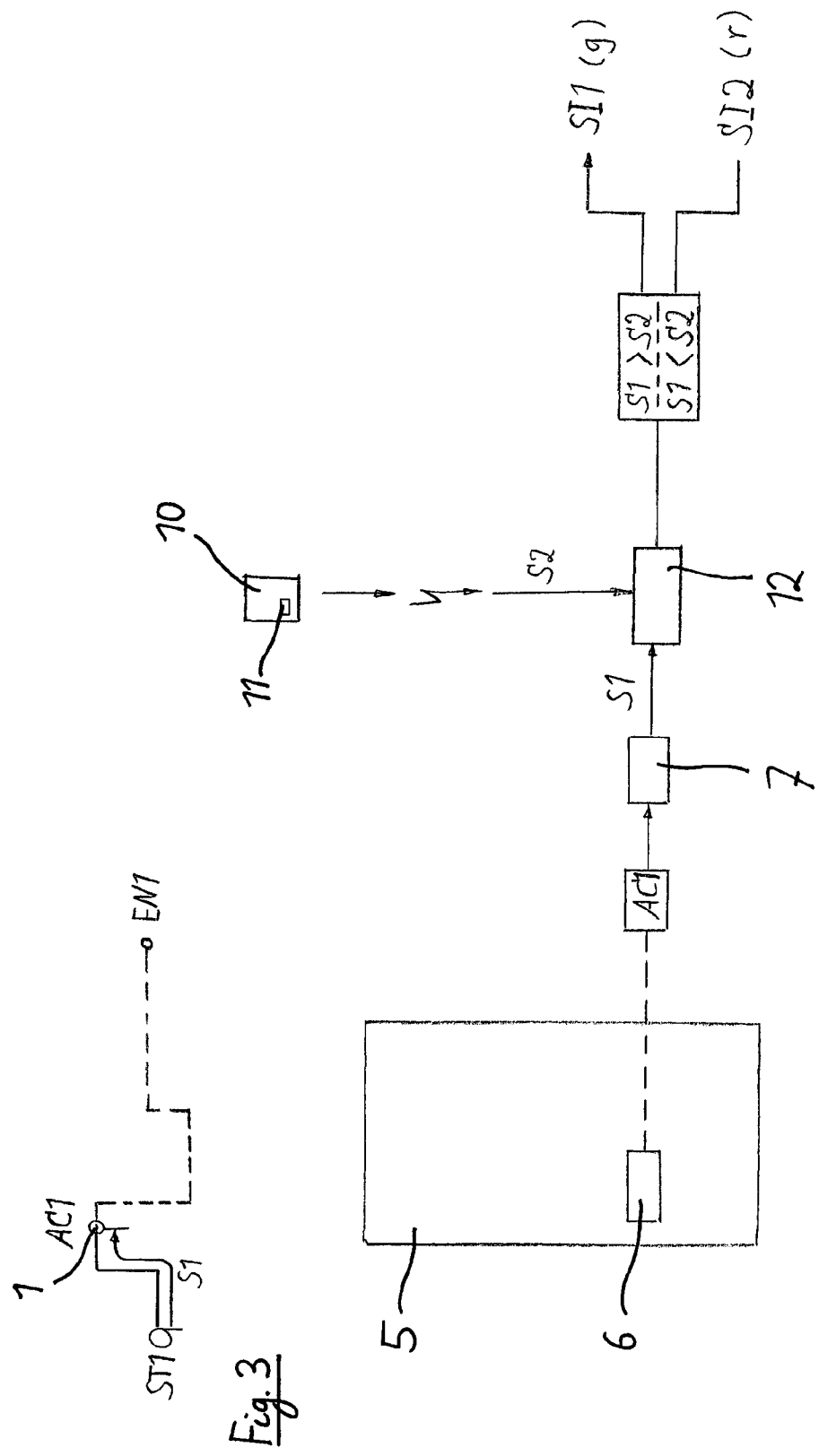

SYSTEM FOR CARRYING OUT A TRAINING OR A COMPETITION OF OR BETWEEN TWO ATHLETES The present application is a 371 of International application PCT/EP2017/000171, filed Feb. 8, 2017, the priority of this application is hereby claimed and this application is incorporated herein by reference.

BACKGROUND OF THE INVENTION

The invention relates to a system for carrying out a training or a competition of or between two athletes.

There is the demand to carry out especially a running training of two runners or to do especially a running competition between two runners not only in the case that the two runners are using the same sports facility and thus that the two runners can observe each other with respect to their actual performance. The mutual observation of the two athletes is not possible in the case that the runners are doing their training remote from another. The same applies with respect to a training or a competition between two athletes of another kind, like e.g. bicyclists or skier.

Thus, it is an object of the present invention to provide a system which makes it possible to allow a mutual observation of the actual performance of the athletes even in the case that the athletes are (far) remote from another. Specifically, it should become possible that the two athletes observe their respective performances during a competition between them.

SUMMARY OF THE INVENTION

The solution of this object according to the invention is characterized in that the system comprises:
  a first sports garment for the first athlete, wherein the first sports garment comprises at least one first signal element for emitting a signal to the first athlete, wherein the first sport garment comprises or is in connection with a first communication element, especially with a first mobile phone, wherein the first communication element comprises a GPS module;
  wherein first control and/or calculating means are arranged at or in the first communication element for measuring of an actual distance covered by the first athlete;
  a second sports garment for the second athlete, wherein the second sports garment comprises at least one second signal element for emitting a signal to the second athlete, wherein the second sport garment comprises or is in connection with a second communication element, especially with a second mobile phone, wherein the second communication element comprises a GPS module;
  wherein second control and/or calculating means are arranged at or in the second communication element for measuring of an actual distance covered by the second athlete;
  wherein the first and the second communication elements are designed to establish a communication between them;
  wherein first control means are provided at or in the first sports garment for emitting a predetermined first signal by the first signal element in the case that the actual distance of the first athlete is bigger than the actual distance of the second athlete and wherein second control means are provided at or in the second sports garment for emitting a predetermined second signal by the second signal element in the case that the actual distance of the first athlete is bigger than the actual distance of the second athlete and
  wherein the predetermined second signal is emitted by the first signal element in the case that the actual distance of the first athlete is smaller than the actual distance of the second athlete and wherein the predetermined first signal is emitted by the second signal element in the case that the actual distance of the first athlete is smaller than the actual distance of the second athlete.

The mentioned first and second communication elements are preferably mobile phones, but also other comparable elements can be taken into consideration which can establish a wireless communication between them.

Thus, the concept according to the invention is basing insofar on the use of communication element, especially of mobile phones, with a respective GPS module by which it is possible to calculate the actual (running) distance (from a defined starting point) which is covered by each of the two athletes, i.e. the distance from a starting point to an actual location of the athletes. This information is used to make a comparison between the two athletes, i.e. which one of the athletes has covered the bigger distance from a starting point. According to this comparison a signal it emitted by the signal means to both athletes, i.e. a first signal to the athlete who covered the longer distance and a second signal (which is different from the first signal) to the athlete who covered the shorter distance so far.

As the communication takes place preferably via the two mobile phones the two athletes can do their competition at different places around the world, i.e. there is no necessity to use the same sporting facility.

By doing so, the two athletes can compare their performances, i.e. there is a permanent signaling who is the "faster" and who is the "slower".

The concept according to the invention can also be used for a comparison of the (running) speed of the two athletes (instead of comparing the covered distances from a starting point). In this case the system comprises basically the same elements, wherein now first control and/or calculating means are arranged at or in the first communication element for measuring of an actual speed of the first athlete and wherein second control and/or calculating means are arranged at or in the second communication element for measuring of an actual speed of the second athlete,
  wherein first control means are provided at or in the first sports garment for emitting a predetermined first signal by the first signal element in the case that the actual speed of the first athlete is bigger than the actual speed of the second athlete and wherein second control means are provided at or in the second sports garment for emitting a predetermined second signal by the second signal element in the case that the actual speed of the first athlete is bigger than the actual speed of the second athlete and
  wherein the predetermined second signal is emitted by the first signal element in the case that the actual speed of the first athlete is smaller than the actual speed of the second athlete and wherein the predetermined first signal is emitted by the second signal element in the case that the actual speed of the first athlete is smaller than the actual speed of the second athlete.

So, the actual (running) speeds of the two athletes (especially runners) can displayed or signaled to the two athletes, i.e. who is actually the faster and who is the slower.

The first control means and/or the second control means can be designed to emit no or a predetermined third signal (distinct from the first and from the second signal) by the first and/or second signal element in the case that the actual distance of the first athlete and the actual distance of the second athlete are equal, taking into account a predetermined tolerance of the ratio between the actual distance of the first athlete and the actual distance of the second athlete (or a predetermined absolute difference between the covered distances). By doing so the signaling of the actual performance is homogenized which can be beneficial if the two athletes provide similar performances. Specifically, it can be provided in this case that the ratio between the actual distance of the first athlete and the actual distance of the second athlete for determination of the tolerance is between 0.9 and 1.1, preferably between 0.95 and 1.05, specifically preferred between 0.99 and 1.01 (or alternatively that the absolute difference between the covered distances is e.g. 50 m, 20 m or 10 m as a tolerance).

A further development of the proposed concept suggests that the predetermined first signal and/or the predetermined second signal depend on the difference between the actual distance of the first athlete and the actual distance of the second athlete. Thus, in this case the emitted signals can vary in their intensity in dependence of the mentioned difference. This can give a hint to the athletes how big the difference in their performances is. Here, the intensity of the (light) signal can be taken into consideration (more or less light intensity dependent of the difference in the performances of the two athletes). Alternatively, a periodical interruption for the light signal in dependency on the difference in the performances of the two athletes can be provided. The frequency of the interruption can increase with the magnitude of the mentioned difference. Also the color of the light can change (the bigger the distance gets the "darker" the green or red light becomes, see below).

When it comes to the survey of speeds (instead of covered distances) it can be provided in an analogue manner that the first control means and/or the second control means are designed to emit no or a predetermined third signal by the first and/or second signal element in the case that the actual speed of the first athlete and the actual speed of the second athlete are equal, taking into account a predetermined tolerance of the ratio between the actual speed of the first athlete and the actual speed of the second athlete. Here, the ratio between the actual speed of the first athlete and the actual speed of the second athlete for determination of the tolerance can be between 0.9 and 1.1, preferably between 0.95 and 1.05, specifically preferred between 0.99 and 1.01.

The predetermined first signal and/or the predetermined second signal can also here depend on the difference between the actual speed of the first athlete and the actual speed of the second athlete.

The first and/or the second sports garment can have a receiving chamber or holding device for receiving or holding the communication element (mobile phone).

The first signal element and/or the second signal element can be signal elements which can emit an optical signal. Preferably, the first signal element and/or the second signal element are an optical fiber, a glass fiber or an electroluminescent element which is fixed to the sports garment.

The first and/or the second sports garment can be sports jackets. The first signal element and/or the second signal element can be fixed in this case to arm sleeves of the sports jacket. This makes it easy for the athletes to observe the emitted signals.

The first control and/or calculating means and/or the second control and/or calculating means can be integrated into the first and/or second communication elements (mobile phones).

Beneficially, the predetermined first signal is a green (or blue) light; the predetermined second signal is preferably a red light. So, it is easily to see for the athlete if he or she is the faster or the slower one.

The first control means can be integrated in the first communication element (mobile phone) and the second control means can be integrated in the second communication element (mobile phone). Here, it is preferred that those functions are available via an App (software application) stored in the communication element (mobile phone).

While a jacket, especially a running jacket, or the like is preferred it is however also possible to apply the concept according to the present idea to other garments like for example a (running) shirt, vest, trousers or the like.

To avoid a frequent switching between the mentioned first and second signals it can be taken into consideration—as described above—that a tolerance is used for the calculation of the signals. In this case the last signals are kept until the mentioned tolerances for the covered distances or speeds are left. The status within the mentioned tolerance can be signaled to the athletes by emitting a third signal, especially a third color. That is, the predetermined first, second and third signals are distinct from another.

That is, for example a green light signal can be emitted to the first athlete if he or she is the athlete who has covered the bigger distance from his or her starting point; at the same time a red light signal is emitted to the second athlete who covered the smaller distance from his or her starting point. If the covered distances are basically equal or within the mentioned tolerance a blue light signal can be emitted to both athletes showing that they have currently the same performance.

The communication between the communication element (mobile phone) and the rest of the devices in the garment occurs preferably wireless. The connection means comprise preferably elements for establishing a Blue Tooth connection which needs not to be described in detail here as it is well known in the art.

Each one single light emitting element can be arranged in the left and in the right region of the garment. The garment has preferably two arm sleeves which reach down at least to the elbow of the athlete.

The survey of the data (covered distance or speed) takes place continuously so that changes can be displayed to the athletes immediately.

Thus, the invention is basing on the idea that two communication elements, which are preferably smart phones, with respective GPS navigation function are used to determine actual covered distances during training or competition or actual speeds of the athletes and to display to both athletes who is the faster and who is the slower athlete. As the communication between the athletes takes place via the communication element (mobile phone) it becomes possible to do competitions or challenges, wherein the two athletes are doing their sports at far distanced locations, e.g. in different towns.

Beneficially, two distinct optical elements (optical fibers/glass fibers/electroluminescent element) are anchored in the garments on the sleeves of the same to make the displayed information visible to the athletes in an easy manner.

The optical elements can be connected with a Blue Tooth device which communicates with the respective communication element (smart phone) which is worn during sporting.

According to the situation and controlled by the communication element (smart phone) light is emitted into the distinct optical fibers by a control element which gets its information via Blue Tooth from the communication element (smart phone).

The proposed system is beneficially used in connection with a running training or a running competition of or between two runners. But it is of course also suitable for other athletes doing a training or competition, especially for bicyclists, skier or walker.

BRIEF DESCRIPTION OF THE DRAWING

In the drawings an embodiment of the invention is shown.

FIG. 3 shows schematically a course which is taken by the first runner and FIG. 4 shows schematically some of the components of a system according to the invention and the function of the same.

DETAILED DESCRIPTION OF THE INVENTION

Figure 1:
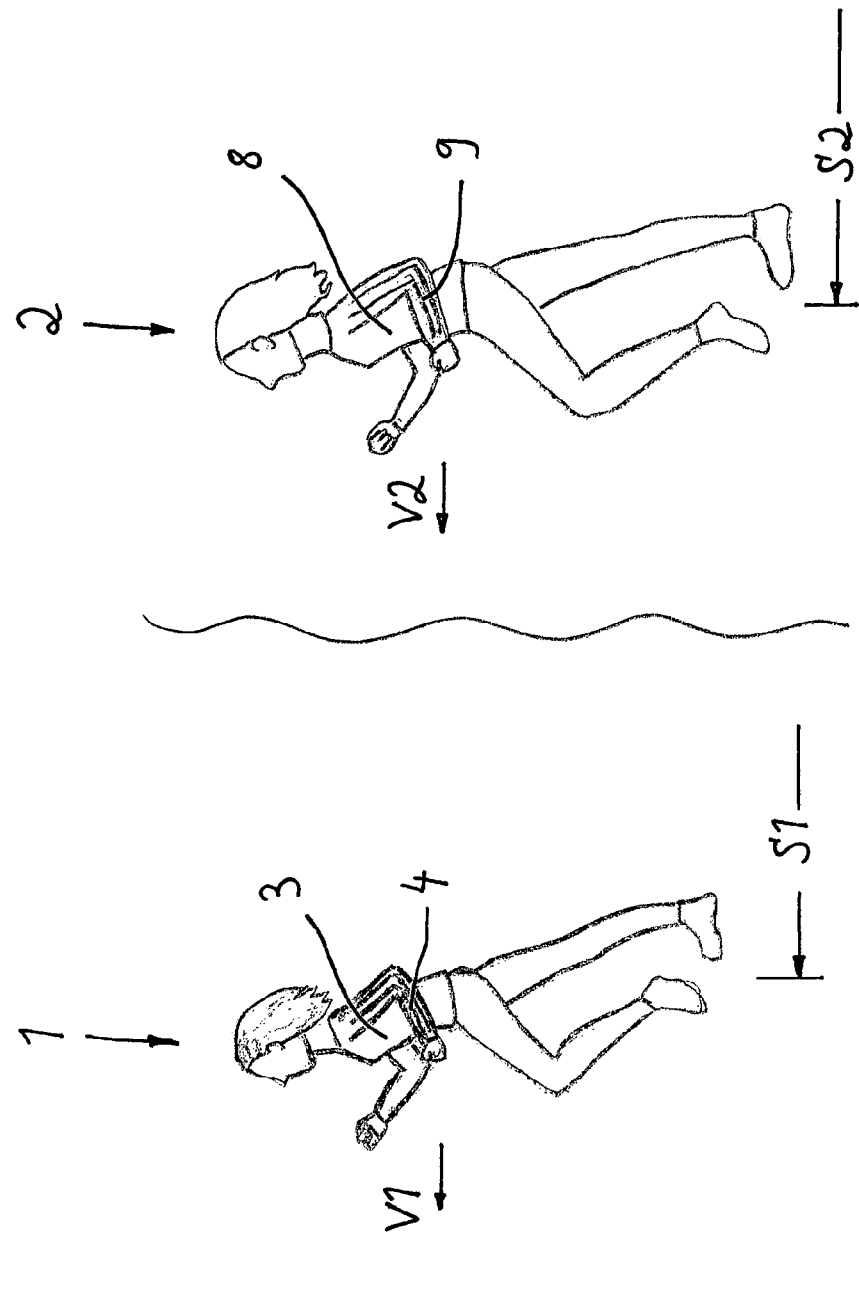
FIG. 1 shows two runners who do a running competition at far distanced locations.

In FIG. 1 two runners 1 and 2 are depicted who wear a first sports garment 3 and a second sports garment 8 respectively. The two runners 1, 2 are running at far distanced locations, i.e. In different towns and would like to carry out a running competition.

With respect to FIG. 3 (there showing the situation for the runner 1) the runners started their competition at an individual start position (ST1) and are running a defined course leading from the start position to an end position (EN1). At a certain time the runner are located at an actual position (AC1). Till this position the runner covered an actual running distance S1 (runner 1) and S2 (runner 2) respectively. Furthermore, the actual running speeds are V1 for the runner 1 and V2 for the runner 2.

Both sports garments 3, 8 are equipped with signal elements 4 and 9. The first signal element 4 is attached or integrated into the first garment 3, while the second signal element 9 is attached or integrated into the second garment 8. In the shown embodiment the signal elements 4, 9 are glass fibers which can display a light signal with a desired color.

Figure 2:
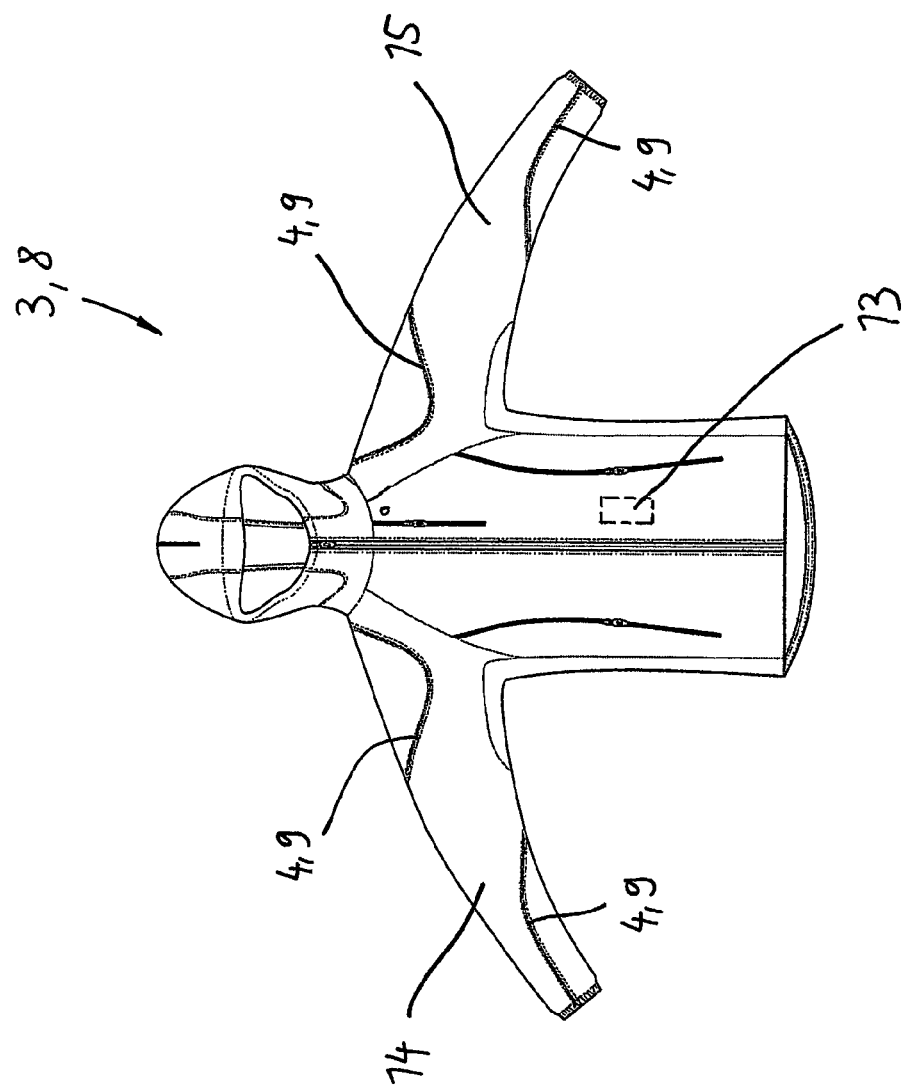
FIG. 2 shows the front view of a sports garment being a running jacket.

This is shown in FIG. 2. Here the sports garment 3, 8 being a runner's jacket is shown which has two (long) arm sleeves 14 and 15. In the inner of the garment 3, 8 a receiving chamber 13 is arranged in which a mobile phone can be inserted. The light emitting element 4, 9 being an optical fiber is arranged in the garment 3, 8 (or two separate light emitting elements) which extend in the sleeve region of the garment 3, 8.

In FIG. 4 the principle of the function of the described system is depicted.

Both garments 3, 8 are in communication with a mobile phone 5 and 10. A first mobile phone 5 is arranged in or at the first garment 3, a second mobile phone 10 is arranged in or at the second garment 8. Each mobile phone 5, 10 has a GPS module 6, 11.

Due to the GPS module 6, 10 it is easy to determine the actual position AC1 (see FIG. 3) of the runner. Control and/or calculating means 7 obtaining the actual position AC1 can calculate the actual covered distance (knowing the route which the runner takes via a respective street map) of the runner from the start position ST1, i.e. the actual running distance S1. This observation/calculation is carried out for both runners 1, 2 as schematically shown in FIG. 4. Thus, the actual running distances S1 and S2 are on hand and can be compared in control means 12.

Basically both garments 3, 8 can be equipped with control means 12 (first and second control means), wherein a transfer of the actual running distances S1 and S2 takes place via the mobile phones (depicted in FIG. 4 with the flash).

Now, as shown in FIG. 4 for the first garment 3 both actual running distances of the two runners 1, 2 are available to make a comparison (S1>S2 or S1<S2). In dependence of this comparison the control means 12 emit a predetermined first signal S11 (for example a green light "g") in the case of S1>S2 or emit a predetermined second signal S12 (for example a red light "r") in the case of S1<S2 to the first signal element (glass fiber). The runner 1 can easily observe the color of the light of the glass fibers of his or her garment and knows if he or she is the "faster" or "slower" runner, compared with runner 2. The respective other signal is displayed at the garment of the runner 2 so that he or she have basically the same information.

As mentioned above no signal or a predetermined third light signal (for example a blue light) can be emitted in the case if both runners have covered so far a substantially equal distance. Here a tolerance can be taken into account to avoid a frequent switching between the first and second signal.

The mobile phone 5, 10 can communicate via connection means (being for example a Blue Tooth connection) with the control and/or calculating means 7.

For displaying the respective light the control means 12 have a light emitting diode (LED). The LED is connected with the signal element 4, 9. The LED is specifically designed to emit light of different colors according to the above explained requirements.

For doing a challenge or competition the two runners can arrange for the competition by the mobile phones for which a respective App (software application) can be used to facilitate the arrangement. For example it can be agreed on a running distance of 5 km from the respective start positions (ST1) which are of course different for the two runners. The runner with the actual better performance receives the "green light", the slower one the "red light". This changes accordingly if the performances are changing.

The Idea is described so far for signaling of the actual covered distance S1 from a start position ST1.

In a similar manner a signal can be emitted basing on a comparison of the actual running speed V1 and V2 of the two runners 1, 2. In this case a respective signal is emitted to both runners who is actually the faster (green light) and who is the slower (red light).

REFERENCE NUMERALS

1 Athlete (runner)
2 Athlete (runner)
3 First sports garment
4 First signal element
5 First communication element (first mobile phone)
6 GPS module
7 First control and/or calculating means
8 Second sports garment
9 Second signal element
10 Second communication element (second mobile phone)
11 GPS module
12 First control means 13 Receiving chamber
14 Arm sleeve
15 Arm sleeve
S1 Actual (running) distance of first athlete (runner)
S2 Actual (running) distance of second athlete (runner)
V1 Actual (running) speed of the first athlete (runner)
V2 Actual (running) speed of the second athlete (runner)
S11 Predetermined first signal
S12 Predetermined second signal
ST1 Start position of athlete (runner) 1
EN1 End position of athlete (runner) 1
AC1 Actual position of athlete (runner) 1

The invention claimed is:

1. System for carrying out a training or a competition of or between two athletes, especially runners, wherein the system comprises:
a first sports garment for the first athlete, wherein the first sports garment is a first sports jacket that comprises at least one first signal element for emitting a signal to the first athlete, wherein the first signal element is an optical fiber, a glass fiber, or an electroluminescent element which is configured to emit an optical signal and which is fixed to an arm sleeve of the first sports jacket so as to run in a longitudinal direction of the arm sleeve and so as to be visible to the first athlete, wherein the first sports jacket comprises or is in connection with a first communication element being a first mobile phone, wherein the first mobile phone comprises a GPS module;
wherein first calculating means are arranged in the first mobile phone for measuring of an actual distance covered by the first athlete;
a second sports garment for the second athlete, wherein the second sports garment is a second sports jacket that comprises at least one second signal element for emitting a signal to the second athlete, wherein the second signal element is an optical fiber, a glass fiber, or an electroluminescent element which is configured to emit an optical signal and which is fixed to an arm sleeve of the second sports jacket so as to run in a longitudinal direction of the arm sleeve and so as to be visible to the second athlete, wherein the second sports jacket comprises or is in connection with a second communication element being a second mobile phone, wherein the second mobile phone comprises a GPS module;
wherein second calculating means are arranged in the second mobile phone for measuring of an actual distance covered by the second athlete;
wherein the first and the second mobile phones are designed to establish a communication between them;
wherein first control means are provided at or in the first sports jacket for emitting a predetermined first signal by the first signal element in the case that the actual distance of the first athlete is bigger than the actual distance of the second athlete and wherein second control means are provided at or in the second sports jacket for emitting a predetermined second signal by the second signal element in the case that the actual distance of the first athlete is bigger than the actual distance of the second athlete; and
wherein the predetermined second signal is emitted by the first signal element in the case that the actual distance of the first athlete is smaller than the actual distance of the second athlete and wherein the predetermined first signal is emitted by the second signal element in the case that the actual distance of the first athlete is smaller than the actual distance of the second athlete, wherein the first control means and the second control means are designed to emit no or a predetermined third signal by the first and second signal element in the case that the actual distance of the first athlete and the actual distance of the second athlete are equal, taking into account a predetermined tolerance of the ratio between the actual distance of the first athlete and the actual distance of the second athlete so as to provide a calming effect on the signals to avoid a frequent switching between the first and second signal, wherein the ratio between the actual distance of the first athlete and the actual distance of the second athlete for determination of the tolerance is between 0.9 and 1.1.

2. The system according to claim 1, wherein the ratio between the actual distance of the first athlete and the actual distance of the second athlete for determination of the tolerance is between 0.95 and 1.05.

3. The system according to claim 2, wherein the ratio is between 0.99 and 1.01.

4. The system according to claim 1, wherein the predetermined first signal and/or the predetermined second signal depend on the difference between the actual distance of the first athlete and the actual distance of the second athlete.

5. The system according to claim 1, wherein the first and/or the second sports garment have a receiving chamber or holding device for receiving or holding the communication element.

6. The system according to claim 1, wherein the first control and/or calculating means and/or the second control and/or calculating means are integrated into the first and/or second communication element.

7. The system according to claim 1, wherein the predetermined first signal is a green light and the predetermined second signal is a red light.

8. The system according to claim 1, wherein the first control means are integrated in the first communication element and the second control means are integrated in the second communication element and are available via an App stored in the communication element.

9. A system for carrying out a training or a competition of or between two athletes, especially runners, wherein the system comprises:
a first sports garment for the first athlete, wherein the first sports garment is a first sports jacket that comprises at least one first signal element for emitting a signal to the first athlete, wherein the first signal element is an optical fiber, a glass fiber, or an electroluminescent element which is configured to emit an optical signal and which is fixed to an arm sleeve of the first sports jacket so as to run in a longitudinal direction of the arm sleeve and so as to be visible to the first athlete, wherein the first sports jacket comprises or is in connection with a first communication element being a first mobile phone, wherein the first mobile phone comprises a GPS module;
wherein first calculating means are arranged in the first mobile phone for measuring of an actual speed of the first athlete;
a second sports garment for the second athlete, wherein the second sports garment is a second sports jacket that comprises at least one second signal element for emitting a signal to the second athlete, wherein the second signal element is an optical fiber, a glass fiber, or an electroluminescent element which is configured to emit an optical signal and which is fixed to an arm sleeve of the second sports jacket so as to run in a longitudinal direction of the arm sleeve and so as to be visible to the second athlete, wherein the second sports jacket comprises or is in connection with a second communication element being a second mobile phone, wherein the second mobile phone comprises a GPS module;

wherein second calculating means are arranged in the second mobile phone for measuring of an actual speed of the second athlete;

wherein the first and the second mobile phones are designed to establish a communication between them;

wherein first control means are provided at or in the first sports jacket for emitting a predetermined first signal by the first signal element in the case that the actual speed of the first athlete is bigger than the actual speed of the second athlete and wherein second control means are provided at or in the second sports jacket for emitting a predetermined second signal by the second signal element in the case that the actual speed of the first athlete is bigger than the actual speed of the second athlete; and wherein the predetermined second signal is emitted by the first signal element in the case that the actual speed of the first athlete is smaller than the actual speed of the second athlete and wherein the predetermined first signal is emitted by the second signal element in the case that the actual speed of the first athlete is smaller than the actual speed of the second athlete, wherein the first control means and the second control means are designed to emit no or a predetermined third signal by the first and second signal element in the case that the actual speed of the first athlete and the actual speed of the second athlete are equal, taking into account a predetermined tolerance of the ratio between the actual speed of the first athlete and the actual speed of the second athlete so as to provide a calming effect on the signals to avoid a frequent switching between the first and second signal, wherein the ratio between the actual speed of the first athlete and the actual speed of the second athlete for determination of the tolerance is between 0.9 and 1.1.

10. The system according to claim 9, wherein the ratio between the actual speed of the first athlete and the actual speed of the second athlete for determination of the tolerance is between 0.95 and 1.05.

11. The system according to claim 10, wherein the ratio is between 0.99 and 1.01.

12. The system according to claim 9, wherein the predetermined first signal and/or the predetermined second signal depend on the difference between the actual speed of the first athlete and the actual speed of the second athlete.

* * * * *